US006497576B1

(12) United States Patent
Smith

(10) Patent No.: US 6,497,576 B1
(45) Date of Patent: Dec. 24, 2002

(54) REACTION TEST

(75) Inventor: Rachel Smith, Surbiton (GB)

(73) Assignee: The Old School Limited, Warwickshire (GB)

( * ) Notice: Subject to any disclaimer, the term of this patent is extended or adjusted under 35 U.S.C. 154(b) by 97 days.

(21) Appl. No.: 09/694,611

(22) Filed: Oct. 23, 2000

(51) Int. Cl.[7] .............................. A61B 5/00; G09B 19/00
(52) U.S. Cl. ...................... 434/236; 434/118; 128/897; 600/558
(58) Field of Search ................................ 434/322, 350, 434/362, 112, 118, 236–238, 262; 600/300, 301, 558; 128/897–898; 351/200; 273/445, 459–461

(56) References Cited

U.S. PATENT DOCUMENTS 6,120,298 A * 9/2000 Jenkins et al. ............... 434/236
6,334,778 B1 * 1/2002 Brown ......................... 434/258
6,368,111 B2 * 4/2002 Legarda ....................... 434/236

* cited by examiner

Primary Examiner—Kevin Shaver
Assistant Examiner—Michael Astorino
(74) Attorney, Agent, or Firm—Kilpatrick Stockton LLP

(57) ABSTRACT

A reaction test for determining the reaction of humans to change consists of a moving shape which changes from time to time, the change being signalled by a person being tested, and apparatus recording the delay between the change and the subsequent signal. The moving shape increases speed during the test, and the chance may be a chance of shape/colour or any other detectable change. The test results are useful in detecting or confirming certain medical conditions.

17 Claims, 1 Drawing Sheet

REACTION TEST

FIELD OF THE INVENTION

This invention relates to a reaction test for humans, and particularly to a screen based reaction test, the results of which may be useful in subsequent assessment diagnosis of the human condition.

BACKGROUND OF THE INVENTION

Tests which measure the speed of reaction of a human to sudden change are well known. Generally speaking such tests categorize humans as fast and slow, the threshold between these categories being indicative of an ability to be suitable for a given task. For example humans selected for dangerous jobs might be required to show a rapid reaction to a sudden change.

Typically such prior art tests may consist of a lamp switching on or off, the reaction time being determined electronically by measuring the delay between the change of state of the lamp and the activation of a switch by the subject of the test. Security forces may use a pop-up target which appears for a limited time, and during which the subject must react, for example by aiming and firing a weapon.

Such tests provide a crude and simple means of placing humans into one of two groups, and the threshold can be varied with relative ease to select individuals with preferred reaction time.

BRIEF SUMMARY OF THE INVENTION

The present invention provides a screen based reaction test adapted to give more detailed information concerning reaction times, and which may be useful in the subsequent assessment, diagnosis, treatment and/or therapy of an individual.

According to a first aspect of the invention there is provided apparatus for providing a test for humans, the apparatus comprising a device which provides a visual shape which is perceived to be moving along a path at varying speed by the human undergoing the test, the apparatus being arranged to vary the visual shape at a plurality of points along the path, and signalling means to be operated by the human undergoing the test as each change of shape is perceived.

Such a test requires a number of human inputs corresponding to each change of shape and permits a series of reaction times to be determined. each reaction time being the delay between a change of shape and the operation of the signalling means.

The speed of the visual shape along said path preferably increases as it progresses.

Preferably, the device which provides the visual shape comprises a screen on which the shape is displayed. The visual shape preferably moves across the screen along said path.

The signalling means may be in the form of a switch.

The device may be in the form of a computer and monitor, the computer being arranged to produce the visual shape and the monitor providing a screen across which the shape tracks to follow the path. In such a case, the signalling means may comprise a mouse, key board or joystick associated with the computer. The computer preferably receives signals from the mouse for processing to determine reaction times for the human undergoing the test. Data resulting from the test can be held in a memory of the computer for future analysis.

In the preferred embodiment, the shape may change from one predetermined shape to another, for example from a circle to a square, and back again. Animal shapes such as duck, mouse or rabbit may be more attractive to children, and adapted to ensure good compliance with the test protocol. The shapes preferably have approximately equal perception to an average human in a certain age category and the size of one shape may be adjusted relative to the size of another in order to achieve approximately equal perception.

In a preferred embodiment. the device is arranged to produce a visual shape in the form of a circular spot of 5 mm diameter. In that embodiment the square may have a side length of 5 mm.

The device may be arranged to operatic to provide a test of around 90 seconds duration during which time the shape may undergo at least 15 changes arid preferable more than 20 changes. 21 changes of shape are preferred.

The device may be arranged to provide a random duration between each change of shape. Alternatively, a predefined sequence of different time periods between shape changes may be selected.

The device is preferably arranged to increase the speed of movement of the shape along the path continuously through the test, typically from a starting speed of about 10 mm/sec to a finishing speed of about 200 mm/sec. The speed of movement may increase linearly, exponentially or in any other desired manner.

The size and speed of the shape may be related to screen size of a computer monitor. For example a screen size may be defined in terms of pixels (e.g. 664×338 pixels); a shape may be defined in pixels (e.g. a square having a side length of 12 pixels), and speed may be defined as pixels per second (e.g. a slow speed of 20 pixels per second to a fact speed of 800 pixels per second).

This latter arrangement may be more suitable where monitors of different size are used to perform the test, or where the test is driven remotely by a host computer.

According to another aspect of the invention there is provided a method of testing the reaction time of a human being to a visual stimulus, the method comprising the steps of providing a visual shape which the human undergoing the test will perceive to be moving alone a path at varying speed, varying the visual shape at a plurality of points along the path, and providing signalling means for operation by the human throughout the test as each change of shape is perceived.

The operation of the signalling means enables the delay between a change of shape and the operation of the signalling means to be determined for subsequent analysis. The method also permits slow or false operation of tie signalling means to be identified according to time thresholds. For example reaction time is classified as normal if within a first time period, slow if within a second time period greater than tile first period, and false if within a third time period greater than the second time period. The third time period ends at the next change of shape; that is to say the time periods are reset from catch change of shape. The first time period may be less that 50 ms, the second time period may be 50.100 ms, and the third time period may be more than 100 ms.

The method may include the step of requiring the human undergoing the test to perform the test at least twice and determining the time delays for the second or subsequent test only.

In the preferred embodiment a screen based reaction test for humans is provided for use with a monitor and switch, the test consisting of an artefact moving across a screen of the monitor for a predetermined period, the speed of movement of the artefact increasing from the beginning of the test to the end, and the artefact undergoing a plurality of changes of shape between the beginning and end of the test, a human operating said switch as each change of shape is perceived.

Such a test stimulates the required multiple human inputs corresponding to each change of shape, and permits a series of reaction times to be determined electronically, each reaction time being the delay between a change of shape of artefact and operation of the switch.

In the preferred embodiment the shape of the artefact alternates between two predefined shapes, for example a circle and a square. The shapes of artefact chosen preferably have approximately equal perception to an average human, and tile size of one artefact may be adjusted relative to the size of another artefact in order to achieve approximately equal perception.

According to a third aspect of the invention there is provided a computer, monitor and mouse in combination, the computer being caused to create an artefact moving across the screen of the monitor for a predetermined period, the artifact changing shape at intervals of not less than 1 second and not more than 10 seconds and the artefact increasing speed from the beginning of the test to the end of the test, and the computer having a memory to record the time of each change of shape of the artefact, and the time of a next subsequent input from said mouse, said times and corresponding inputs being stored in said memory for future analysis.

According to a fourth aspect of the invention there is provided an Internet site adapted to download a test correspondent, to the aforesaid method of testing the reaction time of a human being to a visual stimulus, the Internet site being adapted to receive and temporarily store the address of a human performing the test, to receive and temporarily store the results of the test and to e-mail the stored information to an operator of the Internet site.

According to a fifth aspect of the invention there is provided a computer program for providing a screen based reaction test for a personal computer and having the characteristics of the method aforesaid.

Other features of the invention will be apparent from the following description of a preferred embodiment, illustrated by way of example only with reference to the accompanying drawings in which:

DETAILED DESCRIPTION OF PREFERRED EMBODIMENT

Figure 1:
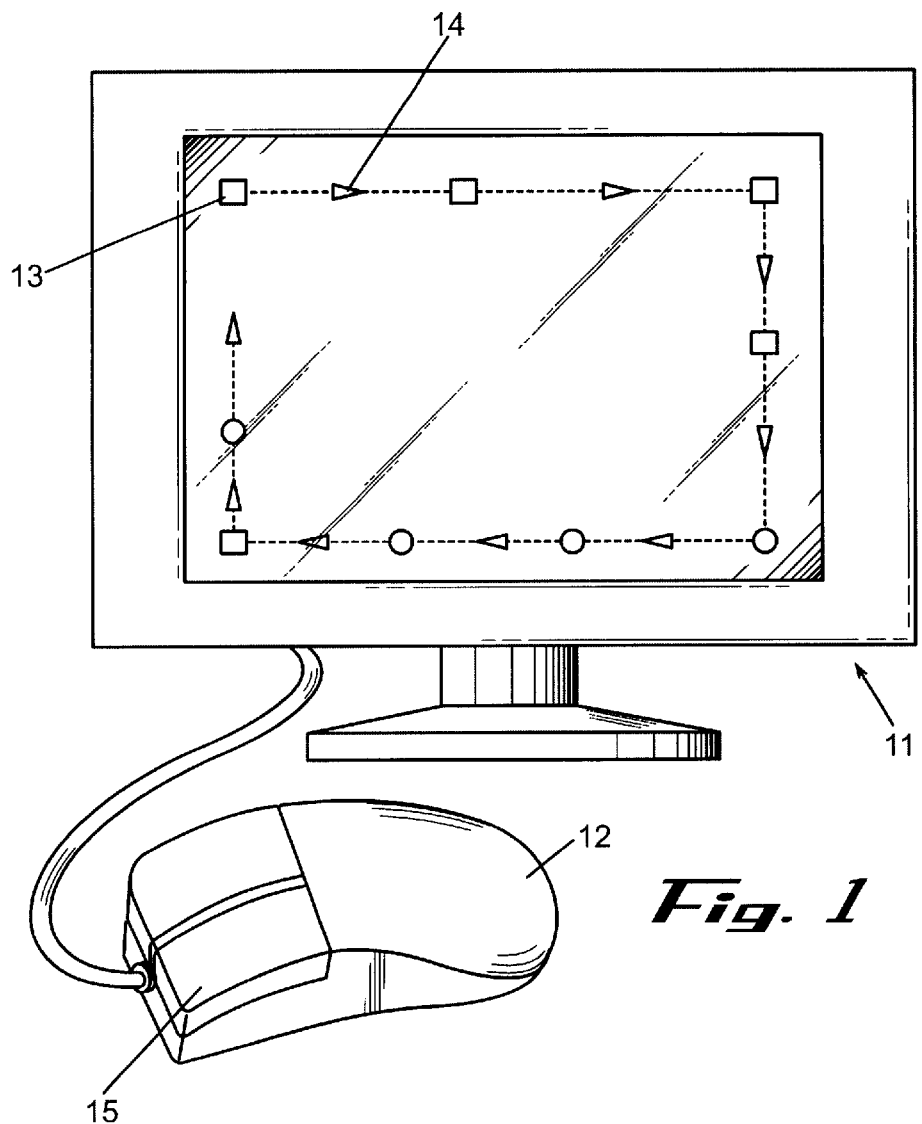
FIG. 1 illustrates a monitor and mouse for use with the invention.

FIG. 1 illustrates a conventional video screen 11, for example the monitor of a personal computer, in association with which the reaction test of the present invention is to be performed. A switch device, for example a mouse 12, permits a user to signal a reaction—as an alternative the switch may for example be the space bar of a keyboard, a foot pedal or the remote control of a television. The user's reaction may signalled by movement or by other means such as sound.

A driver device such as a computer program causes an artefact 13 to track across the screen in the manner indicated by arrows 14. Typically the artefact 13 follows the perimeter of the screen so as to give relatively long periods of unidirectional movement, and on a screen having a diagonal dimension of 400 mm, the shape may follow a track about 30 mm from the screen perimeter.

the driver device causes the artefact 13 to periodically change shape, or example the shape may alternate between circle and square, and the user is required to indicate a reaction to this change by operating the switch 15, for example the left button of the mouse 12. The interval between changes of artefact shape is preferably not less than 1 second and not more than 10 seconds. The artefact may alternatively change.

An important feature of the invention is that the tracking speed increases over the duration of the test for example from around 10 mm/sec to 200 mm/sec. A continuous progressive increase is not essential, but in the preferred embodiment a constant acceleration is provided. The acceleration of the artefact may however also undergo an increasing rate of change, or may change step-wise in increments.

The size of the artefact is such as to be reasonably distinguishable by the user, and for example a screen having a diagonal dimension of 400 mm, typically has a circular artefact of about 5 mm in diameter. Any alternative shape of artefact may be selected, and in the preferred embodiment a 5 mm square is provided, so that the shape chances sequentially from circle to square to circle, and so on.

Other artefacts are possible, it being understood that the greater the perceived change of shape, the easier it will be for the user to rapidly detect the change. For that reason a significant change of area of the artefact, for example from a square to an equilateral triangle, may be more easy to detect than a less significant change, for example from a circle to a square.

The relationship between different shapes of artefact and their impact on reaction time, can be determined empirically from standardized tests, and the relative sizes of artefacts selected so as to eliminate shape effects. For example a greater change of artefact area can be compensated by a reduction in artefact size.

The time of an individual reaction test should be not longer than a reasonable attention span, and in the preferred embodiment is 90 seconds. The test is preferably repeated, and the results of the second test used to calculate certain reaction parameters. In this way the first test is used for familiarization, and to ensure that the user does not give misleading inputs due to misunderstanding of the test protocol. In the preferred embodiment 21 changes of shape are provided at random intervals.

Each change of shape and switch input is recorded, and the reaction time is calculated. Reaction times are categorized as hits and misses, a hit being detection of a switch input within 50 ms of a change of shape. All other inputs are categorized as a miss and categorized as slow (50–100 ms) or false (above 100 ms) and not likely to be in response to a change of shape. The thresholds for distinguishing hits and misses may be varied.

Figure 2:
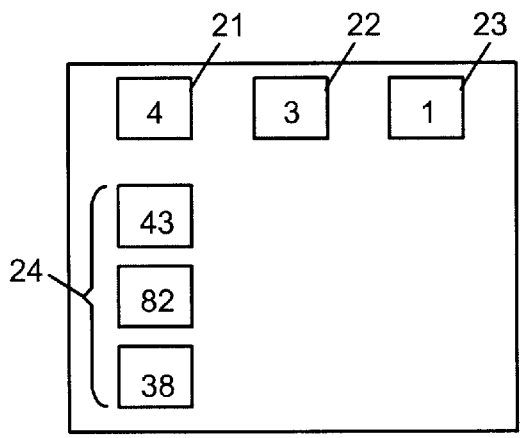
FIG. 2 illustrates results of the reaction test and a preferred tabular form.

The results of the test may be presented in any desired manner, but in the preferred embodiment the following format is provided, as illustrated in FIG. 2.

Firstly an error score 21 is generated, being the total number of misses. A typical human having no significant eye, cognition or learning difficulties will usually have a score of 2 or less. A score 3 or more may indicate an underlying problem for consideration by an analyst.

Two further scores arc also generated, being the number of slow responses 22 and the number of false responses 23.

Individually these latter scores may be useful to an analyst in the event of an overall failure of the test. the reaction time for the 21 changes of shape are averaged in groups of the 7 fastest, the 7 slowest and those remaining. These three averaged reaction times are provided to an analyst, for example in the form of table 24.

Reaction times of less than 50 ms are not considered to be indicative of an underlying problem, and if the 3 averaged values all lie below the 50 ms threshold, the user may not be referred for further treatment.

However if all averaged values are high, for example 80 ms, the user may be suitable for further investigation in relation to dyspraxia (slow but accurate response times).

In cases where one averaged value is high (higher than 50 ms) and the other two are low (less than 50 ms), the user may be exhibiting symptoms of dyslexia and require further investigation.

Other conclusions may be drawn from the pattern of results and the reaction times may be displayed individually or be subjected to mathematical analysis to produce an overall 'score'.

The reaction test of this invention is of greater benefit if the subject can be instructed to follow movement of the artefact by eye movement alone—that is to say without turning the head. In this way potential eye-related problems may be detected, either from observation of the subject or by analysis of the results.

The test of the invention is particularly suitable for use via the Internet since it allows remote monitoring and testing of subjects with readily available and conventional equipment. In practice the subject would log on to a website carrying the test, and follow instructions to permit the test to be performed, perhaps after a practice session. On completion, the test results would be e-mailed to an analyst who would inform the subject of result and whether further investigation was required.

What is claimed is:

1. Apparatus for providing a test for humans, the apparatus comprising a device providing a visual shape which is perceived to be moving along a path at varying speed by the human undergoing the test, the device being operative to vary the visual shape at a plurality of points along the path, and further including signalling means operated by the human undergoing the test as each change of shape is perceived, the device being operative to vary the speed of the shape and to vary the shape independent of operation of the signalling means by the human.

2. Apparatus according to claim 1 wherein the speed of the visual shape along said path increases as the test progresses.

3. Apparatus according to claim 2 wherein the speed of the visual shape increases from less than 10 mm/sec to more than 100 mm/sec.

4. Apparatus according to claim 1 wherein the signalling means is a hand operated switch.

5. Apparatus according to claim 1 wherein the device is a personal computer, the monitor of the computer providing a screen across which the shape moves and the signalling means comprising a computer mouse.

6. Apparatus according to claim 1 wherein the duration of the test is substantially 90 seconds.

7. Apparatus according to claim 1 wherein the shape undergoes 15–25 changes during the test.

8. Apparatus for providing a test for humans, the apparatus comprising a device providing a visual shape which is perceived to be moving along a path at varying speed by the human undergoing the test, the device being operative to vary the visual shape at a plurality of points along the path, and further including signalling means operated by the human undergoing the test as each change of shape is perceived, wherein the device is a personal computer, a monitor of the computer providing a screen across which the shape moves, and the signalling means comprising a computer mouse, and wherein the shape repeatedly changes from a circle to a square, and from a square to a circle.

9. Apparatus according to claim 8 wherein the circle has a diameter of 5 mm and the square has it side length of 5 mm.

10. A method of testing the reaction time of a human to a visual stimulus, the method comprising the steps of providing a visual shape which the human undergoing the test will perceive to be moving along a path at an increasing speed, varying the visual shape at a plurality of points along the path, providing signalling means for operation by the human as each change of shape is perceived, and wherein the increase in speed and variation in visual shape are independent of the signalling means.

11. The method of claim 10 and further comprising the steps of recording the time delay between a change of said visual shape and operation of said signalling means before the next change of shape.

12. The method of claim 11 and further comprising the steps of calculating a test score, said test score being the total number of recorded time delays below predetermined time threshold.

13. The method of claim 10 wherein the visual shape alternates between two alternative shapes.

14. A method of testing the reaction time of a human to a visual stimulus, the method comprising the steps of providing a visual shape which the human undergoing the test will perceive to be moving along a path at an increasing speed, varying the visual shape at a plurality of points along the path, providing signalling means for operation by the human as each change of shape is perceived, setting a test duration, setting an initial speed of movement of the visual shape, setting a final speed of movement of the visual shape, setting the number of changes of shape required, determining an acceleration profile for said visual shape, and determining random time periods between each change of shape, each period being not less than 1 second and not more than 10 seconds.

15. A computer, monitor and mouse in combination, the computer being adapted to control the monitor to create a test producing a visual shape moving across the monitor for a predetermined period, the visual shape changing at intervals and the visual shape increasing speed from the beginning to the end of a test, and the computer having a memory to record the time of each change of the visual shape and the time of the next subsequent input from said mouse.

16. The combination of claim 15 wherein the predetermined period is in the range 60–120 seconds.

17. The combination of claim 16 wherein the intervals are not less than 1 second and not more than 10 seconds.

* * * * *